United States Patent [19]

Bauman

[11] Patent Number: 4,570,614

[45] Date of Patent: Feb. 18, 1986

[54] LARYNGOSCOPE WITH DISPOSABLE BLADE AND LIGHT CONDUCTOR

[76] Inventor: Jack Bauman, 1677 San Onofre Dr., Pacific Palisades, Calif. 90272

[21] Appl. No.: 687,504

[22] Filed: Jan. 4, 1985

Related U.S. Application Data

[63] Continuation of Ser. No. 492,190, May 6, 1983, abandoned.

[51] Int. Cl.$^4$ .............................................. A61B 1/06
[52] U.S. Cl. ...................................................... 128/11
[58] Field of Search .................................... 128/10, 11

[56] References Cited

U.S. PATENT DOCUMENTS

| | | | |
|---|---|---|---|
| 3,598,113 | 8/1971 | Moore | 128/11 |
| 3,826,248 | 7/1974 | Gobels | 128/11 |
| 4,112,933 | 9/1978 | Moses | 128/11 |
| 4,273,112 | 6/1981 | Heine et al. | 128/11 |
| 4,306,547 | 12/1981 | Lowell | 128/11 |

FOREIGN PATENT DOCUMENTS 2147054  4/1973  Fed. Rep. of Germany ........ 128/11

Primary Examiner—Edward M. Coven
Assistant Examiner—Max F. Hindenburg
Attorney, Agent, or Firm—Fulwider, Patton, Rieber, Lee & Utecht

[57] ABSTRACT

The blade of a laryngoscope is made of non-metallic material such as plastic so that it can be economically disposed of after each use. Further, it includes a flexible portion which will protect a patient's teeth as a consequence of the unconscious tendency to encroach upon the patient's upper teeth by using them as a fulcrum for the blade in exposing the larynx in order to insert an endotracheal tube. A light source is located in the handle of the laryngoscope rather than the blade and a light conductor is held by the blade for optically conducting light from the source in the handle to an exit point along the blade for viewing the larynx.

6 Claims, 10 Drawing Figures

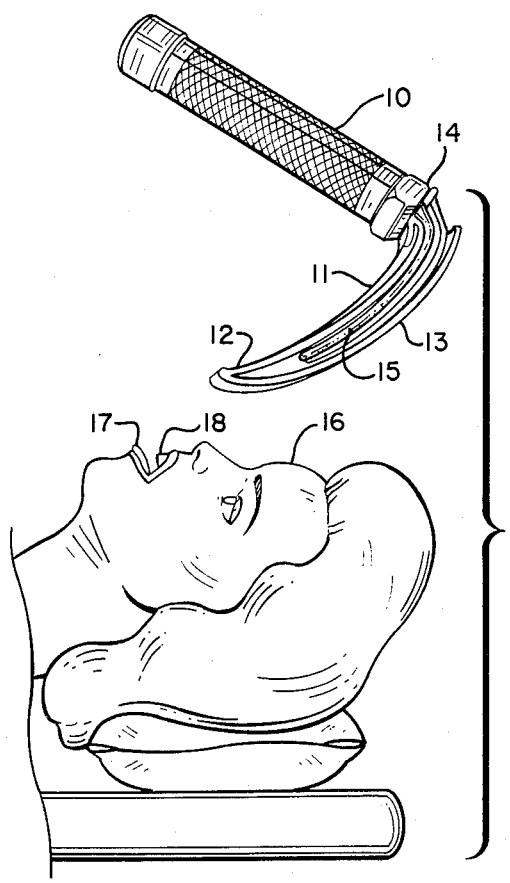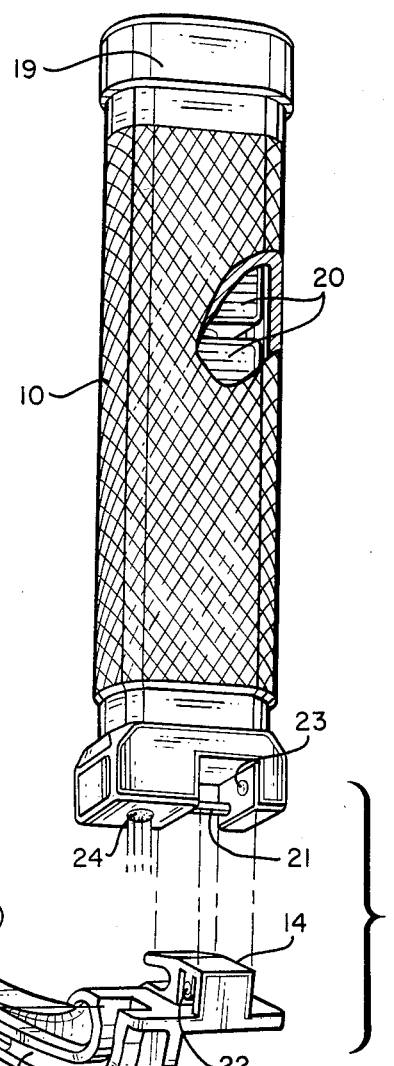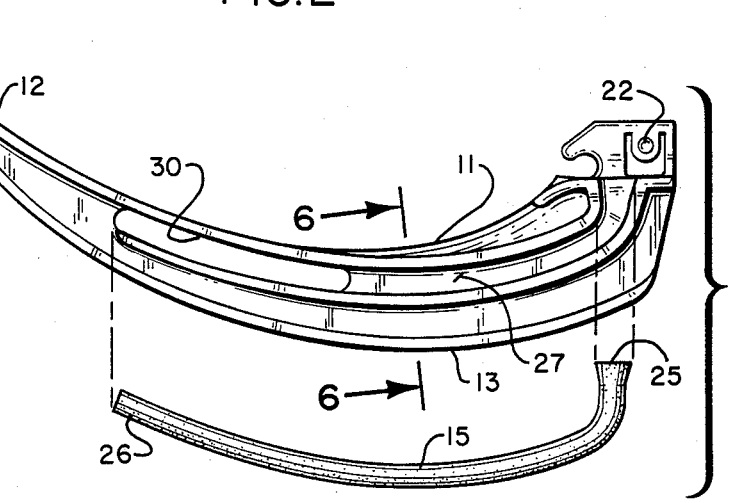
FIG.1
FIG.2
FIG.3
FIG.4

LARYNGOSCOPE WITH DISPOSABLE BLADE AND LIGHT CONDUCTOR

This application is a continuation of application Ser. No. 492,190, filed May 6, 1983, now abandoned.

FIELD OF THE INVENTION

This invention relates generally to medical instruments and more particularly to a laryngoscope having a blade primarily used to facilitate insertion of an endotracheal tube in a patient wherein the blade is disposable.

BACKGROUND OF THE INVENTION

Most laryngoscopes generally comprise a laryngoscope blade and cooperating handle, both made of metal. These two items are connected together to form a general L-shape. The handle normally serves as an enclosure for batteries for energizing an appropriate light bulb secured adjacent to the blade and connected by wires to the batteries in the handle. This bulb illuminates the patient's mouth and larynx entrance areas. A first surface on the blade itself is used to lift the tongue and mandible of a patient when the patient is in a supine position or depress the tongue and mandible of the patient if the patient is in an upright position. This action prevents the patient's tongue from obstructing the channel of vision.

While the instrument is useful for examining the larynx, its primary function is to expose the larynx in a manner to facilitate the insertion of an endotracheal tube. In this respect, the patient usually is in a supine position on an operating table with his or her head extending backwardly. In this position, as described, the first surface of the laryngoscope blade is used to lift the tongue and mandible upwardly to expose the larynx, the light on the blade being positioned beneath the lifting first surface of the blade. A second surface of the blade spaced rearwardly of the first surface is in a position opposing the upper front teeth of the patient.

In using the laryngoscope, there is almost invariably an unconscious tendency to use the upper front teeth of the patient as a fulcrum for the blade in exposing the larynx. Because of the metal construction of the blade, the patient's front teeth often are chipped by such contact and occasionally the teeth may be broken or knocked out.

In addition to the foregoing problems, conventional laryngoscopes should be sterilized after each use, or at a minimum the blade for the laryngoscope must be detached from the handle and sterilized.

In U.S. Pat. No. 3,826,248 there is shown an improved laryngoscope blade wherein that portion of the conventional laryngoscope blade defining the referred to second surface opposing the upper front teeth of the patient is removed and a plastic insert substituted for the removed portion. This plastic insert is of elastic material, capable of flexing in a manner to cushion contact with the patient's upper front teeth should the same be used unconsciously as a fulcrum when manipulating the blade to expose the larynx. This laryngoscope blade further carries a light bulb as in a conventional blade. In one embodiment, however, the light bulb is positioned in the foot of the blade and a fiber optic light conductor is used to direct the light.

While the problem of damaging teeth is solved to a large extent by the above described laryngoscope blade, there still remain problems of added expense in the actual manufacture of the blade when compound materials are used and a light bulb is incorporated in the blade.

U.S. Pat. No. 4,295,465 shows another type blade for a laryngoscope including a flange mechanically pivoted to part of the blade and biased by a spring. This flange is positioned to engage the patient's teeth and cushion action of the blade against the teeth when the teeth are used as a fulcrum.

In my prior U.S. Pat. No. Des. 242,396, I disclose a unique shaping and contouring for a disposable cover to be used to cover a laryngoscope blade. In U.S. Pat. No. 4,037,588 there is shown a disposable laryngoscope blade made entirely of plastic, this plastic material being capable of optically conducting light so that a light bulb can be arranged in the handle juxtaposed to a surface of the plastic blade. In this blade construction, in order to provide proper strength for the portion of the blade that depresses the tongue, the material has had to be fairly thick. As a consequence, the second surface portion opposing the patient's teeth corresponding to that described for conventional blades is also relatively rigid and thus the problem of damaging the patient's teeth has not been solved by this all plastic blade member.

Finally, in my patent application, Ser. No. 473,040 filed Mar. 7, 1983 and entitled LARYNGOSCOPE WITH DISPOSABLE BLADE now abandoned; and still pending application Ser. No. 472,975 filed Mar. 7, 1983 and entitled LARYNGOSCOPE BLADE AND DISPOSABLE COVER, there are described respectively a disposable laryngoscope blade made entirely of plastic but incorporating features to minimize damage to a patient's teeth, and, a disposable cover for a laryngoscope blade wherein the blade has been modified to receive the cover in such a manner that a flexible portion of the cover is defined for minimizing damage to a patient's teeth.

All the the foregoing is the closest prior art of which I am aware to my present invention.

BRIEF DESCRIPTION OF THE PRESENT INVENTION

With the foregoing in mind, the present invention contemplates an improved laryngoscope in which several of the advantages of prior art laryngoscopes are incorporated without attendant disadvantages.

More particularly, the laryngoscope of the present invention includes an elongated handle and a disposable blade of non-metallic material. In the preferred embodiment a light conductor is held by the material of the blade, this light conductor being made of high quality light transmissive material such as clear plastic. By utilizing a separate light conductor rather than using the non-metallic or plastic material of the blade itself as a light conductor, there is removed any limitation on the particular type of plastic used for the blade and accordingly, an appropriate flexible portion may be more easily formed for cushioning the blade portion normally opposed to the patient's teeth, thereby minimizing damage to the patient's teeth.

As in the case of my heretofore mentioned prior patent application, Ser. No. 473,040 entitled LARYNGOSCOPE WITH DISPOSABLE BLADE, a light bulb is incorporated in the handle of the laryngoscope In the present invention, however, the mechanism for automatically energizing the light bulb is greatly simplified over prior art arrangements.

The blade itself is detachable from the handle along with the light conductor so that the same is simply disposed or after use so that repeat sterilization is unnecessary.

BRIEF DESCRIPTION OF THE DRAWINGS

A better understanding of the present invention will be had by now referring to the accompanying drawings in which:

FIG. 1 is a side elevational view of the laryngoscope of this invention preparatory to being used on a patient in a supine position;

FIG. 2 is a greatly enlarged ¾ rear perspective view of the laryngoscope of FIG. 1 showing certain portions in exploded relationship;

FIG. 3 is a fragmentary cross section of a portion of the laryngoscope of FIG. 2;

FIG. 4 is a side elevational view of the laryngoscope blade of FIG. 2 showing a component in exploded relationship thereto;

DETAILED DESCRIPTION OF THE INVENTION

Figure 5:
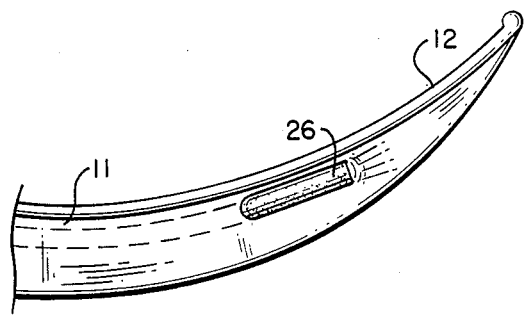
FIG. 5 is a fragmentary elevational view showing a portion of the opposite side of the blade of FIG. 4.

Referring first to FIG. 1 the laryngoscope includes an elongated handle 10. A disposable blade 11 of non-metallic material includes a tongue engaging portion 12 and a flexible portion 13 normally in a position opposing a patient's teeth when the blade is in use. Flexible portion 13 is formed by a structural shaping of that blade portion only opposing the patient's upper teeth permitting flexing as by bending of such portion. Means 14 are provided coupling the blade to one end of the handle 10 for movement from a folded position to an operative position in which the blade defines with the handle a general L-shape.

A light conductor 15 which might comprise clear plastic is held in the blade with a light entrance end positioned to be in optically coupling relationship with an appropriate light source in the one end of the handle 10 when the blade assumes its operative position shown. The other end of the light conductor 15 is positioned so that light from the source in the handle exits along the line of sight of the blade in a direction to illuminate a patient's larynx when the blade is in use.

Thus, still referring to FIG. 1, there is shown a patient 16 in a supine position. The tongue engaging portion 12 of the blade 11 is arranged to depress the patient's tongue and mandible indicated at 17. When the blade is so used, and as described heretofore, there is an unconscious tendency to use the patient's upper teeth indicated at 18 as a fulcrum for the blade, these teeth being engaged by the portion 13 of the blade 11. By making this portion flexible as will be described in greater detail as the description proceeds, the risk of damaging the patient's teeth when utilizing the blade of the present invention is minimized.

It will be understood that because the blade itself is of non-metallic material, it is fairly economical to manufacture. Further, since the light bulb or light source is incorporated in the handle 10, the blade along with the light conductor can be detached from the handle and disposed of after use so that repeated sterilization is unnecessary.

Referring now to FIG. 2, the foregoing as well as further features and advantages of this invention will become evident.

Referring first to the handle 10, it will be noted that the same includes a removable cap 19 at its upper end opposite the one end coupled to the blade 11, for receiving batteries 20.

The coupling means 14 described briefly in FIG. 1 is conventional in certain respects. Thus, the means 14 includes an appropriate cross groove for receiving a pivot rod 21 in the one end of the handle 10. Cooperating dimples and ball detents 22 and 23 may be provided to hold the blade 11 in its operative position wherein it assumes the L-shape configuration shown in FIG. 1.

The light source heretofore referred to in the handle 10 includes a light bulb 24 arranged to project slightly from the undersurface of the one end of the handle 10. Essentially, the light bulb 24 is juxtaposed the entrance end of the light conductor 15 described in FIG. 1. This entrance end is indicated in the exploded view of the light conductor in FIG. 2 at 25. The opposite end of the light conductor 15 from which light exits is shown at 26.

The light conductor 15 shown in FIG. 2 is held to the blade 11 by an appropriate channel 27 formed in a side of the blade immediately beneath the tongue engaging portion 12 of the blade.

Referring to FIG. 3, it will be noted that the one end of the handle includes contact means 28 engaged by the light conductor entrance end 25 bearing against the bulb 24 to urge it upwardly as viewed in FIG. 3 when the blade is coupled about the pivot rod 21 and swung into its operative position. In other words, the light bulb 24 is automatically energized when the blade is folded outwardly to its operative position by action of depressing the bulb 24. In this respect, a small spring 29 would normally bias the bulb 24 downwardly as viewed in FIG. 3 to maintain the contact means 28 open so that the bulb is normally de-energized and will only be energized when the blade is swung to its operative position.

The foregoing feature is importat in that it eliminates the necessity for any type of auxiliary switch. Further, the spring 29 biasing the bulb 24 against the light entrance portion 25 of the light conductor 15 assures a reliable and efficient optical coupling of the light from the bulb into the entrance end of the light conductor.

Referring now to FIG. 4, there is again shown the blade 11 in side elevation with the light conductor 15 exploded away. As will be clear, the channel 27 terminates as it approaches the far end of the blade; that is, the left end as viewed in FIG. 4 in an elongated opening 30. This opening is arranged to receive the far end 26 of the light conductor 15 so that light actually exits from this end on the opposite side of the blade as viewed in FIG. 4. This light is directed along the line of sight of the blade as viewed by the doctor for proper illumination of the patient's larynx.

FIG. 5 shows a fragmentary view of the opposite end of the blade described in FIG. 4 wherein the light conductor 15 is positioned in the blade with its exit end 26 extending through the opening 30. This exit end 26 after having been passed through the opening 30 of the blade is clearly visible in the showing of FIG. 5.

Figure 6:
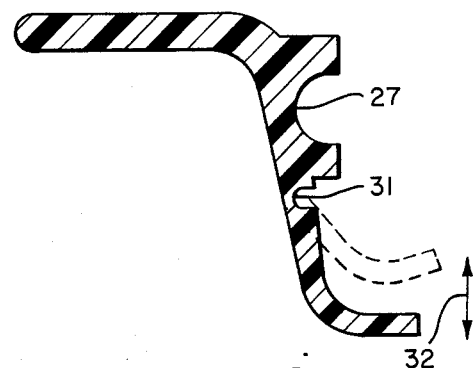
FIG. 6 is a greatly enlarged cross section taken in the direction of the arrows 6—6 of FIG. 4.

Referring to the enlarged cross section of FIG. 6, the cradle or channel 27 for the light conductor 15 is clearly illustrated. Further, it will be noted that the flexible portion 13 normally opposed to the patient's teeth is rendered flexible in the specific embodiment disclosed by making a longitudinal groove 31 in the the wall of the web running between the light conductor 15 when the same is in position and the portion of the blade opposing the patient's teeth. By providing such a groove, there is essentially formed a thinned part of the web of the blade as viewed in cross section permitting flexing of the portion opposing the patient's teeth as indicated by the double headed arrow 32 in FIG. 6, the flexing of the web taking place between the solid and dotted line positions of the flexible portion 13.

Figure 7:
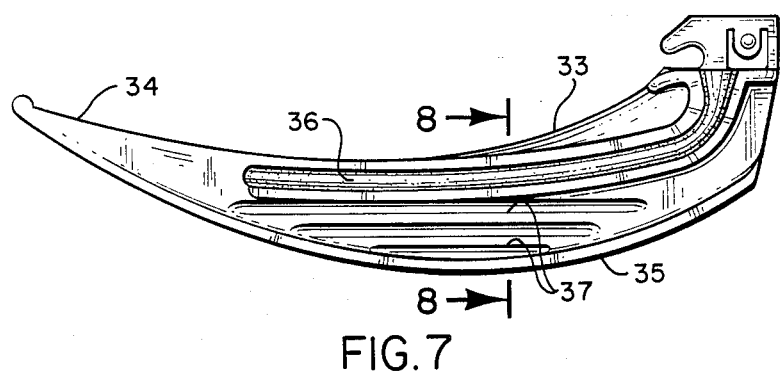
FIG. 7 is a side elevational view of a modified blade illustrating an optional feature of this invention.

Referring to FIG. 7, there is shown another blade somewhat straighter than the blade 11 described in FIG. 4. In this respect, it should be understood that the present invention is applicable to fully straight type blades as well as the curved blades shown. Some examples of straight blades are shown in my copending application Ser. No. 473,040 referred to heretofore.

In FIG. 7, the blade 33 again includes a tongue engaging portion 34 and a flexible portion 35 normally opposing the patient's teeth. Again, there is provided a light conductor 36 held by the blade in a manner similar to the light conductor 15 described in FIG. 4.

Rather than a groove in the wall such as described at 31 to provide flexibility to the portion 35, there is shown in FIG. 7 accordion pleats 37.

Figure 8:
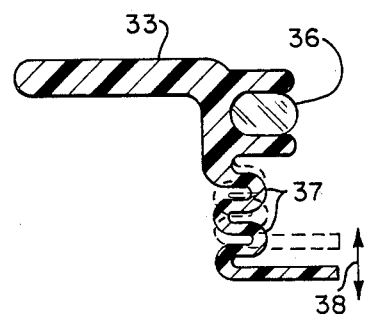
FIG. 8 is a cross section taken in the direction of the arrows 8—8 of FIG. 7.

Referring to the cross section of FIG. 8, these accordion pleats 37 are more evident and will permit a flexing of the portion 35 opposing the patient's teeth in an up and down direction as viewed in FIG. 8 and as indicated by the double headed arrow 38.

Figure 9:
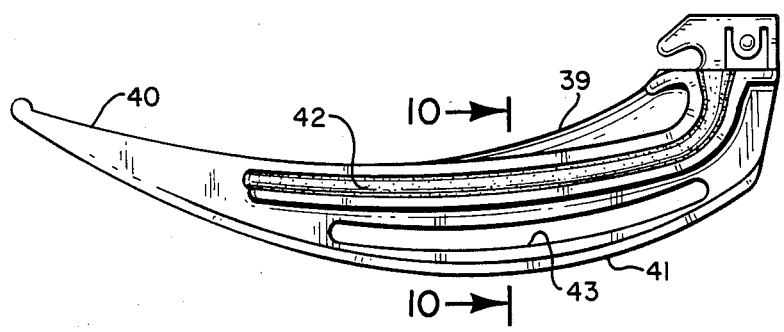
FIG. 9 is a side elevational view of yet another blade incorporating a still further alternative feature in accord with the present invention; and, FIG. 10 is a cross section taken in the direction of the arrows 10—10 of FIG. 9.

FIG. 9 shows yet another blade 39 having a tongue engaging portion 40 and a flexible portion 41 opposing a patient's teeth. Also shown is a light conductor 42 held by the blade 39 in a manner similar to that described for the light conductor 15 of FIG. 4.

In the embodiment of FIG. 9, flexibility is imparted to the portion 41 by forming an elongated window in the web of the blade adjacent to the portion 41 opposing the patient's teeth.

Figure 10:
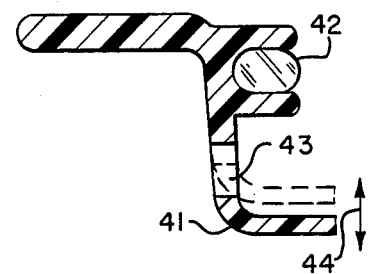

Referring to the cross section of FIG. 10, this window 43 will permit flexing of the portion 41 in an up and down direction as indicated by the double headed arrow 44 as viewed in FIG. 10.

The embodiments of FIGS. 7 through 10 are set forth merely to indicate that this invention is not limited to any one specific means for providing the desired flexibility of the portion of the blade opposing the patient's teeth.

OPERATION

In the initial manufacture of the blade described herein, there are provided two molds. One for the blade 11 and one for the light conductor 15. Afer each piece is molded, it is a simple matter to fit the conductor 15 into the channel 27 of the blade to be held thereby.

With respect to the foregoing, a great advantage is realized by using two separate components and then placing them together. First, there is no limitation as to the type of plastic which can be used for the blade 11. In other words, it is not necessary that this plastic have any particular light transmissive characteristics since the light is transmitted by the light conductor 15 and does not depend on the transmissive characteristics of the plastic for the blade. This advantage means that appropriate plastic material which can be properly worked to provide the desired rigidity for the blade portion engaging the patient's tongue and mandible and the desired flexibility for the blade portion opposing the patient's teeth can readily be realized.

The material for the light conductor 15, on the other hand, can be selected from the highest quality light transmissive clear plastics.

Once the blade and light conductor are assembled, they are appropriately sterilized and packaged.

When the blade is to be used, it is simply removed from the packaging and the means 14 hooked onto the pivot rod 21 described in FIG. 2, the blade then being swung outwardly from the handle to assume its L-shaped position described in FIG. 1. This action automatically results in the light entrance end of the clear plastic shown at 25 engaging the end of the bulb 24 described in FIG. 3 to depress the same against the action of the spring 29. When the ball detents 23 and cooperating dimples 22 register, the bulb 24 is fully depressed so as to close the contacts 28 and energize the bulb. A tight optical contact between the bulb and entrance end of the light conductor is assured as described heretofore.

After the doctor completes his examination or has successfully inserted an endotracheal tube, the blade 11 along with the light conductor is simply decoupled from the handle and thrown away. Inexpensive plastic maaterial exhibiting the desired rigidity and flexibility at various portions can be used for the blade since the light transmissive characteristics of the blade plastic are not a consideration as described. Thus the blade cann be economically manufactured and since it does not incorporate a bulb itself, the disposal of the blade after a single use does not pose any serious economic problem.

As already described, the features of this invention can be incorporated on straight type laryngoscope blades and on smaller versions used with children.

It should be understood that the flexible portion can be formed by simply thinning the material in the area involved in place of or in addition to the provision of the groove or accordian pleating or window. For example, the flexible portion in FIG. 6 is shown as tapering below the groove 31 towards a thinner configuration than the upper portion of the blade used to depress the patient's tongue.

Further, the light conductor can be provided with an exterior coating except at its light entrance and exit ends, to minimize light scattering.

The present invention, accordingly, is not to be thought of as limited to the exact blade shapes and structures described merely for illustrative purposes.

I claim:

1. A non-metallic laryngoscope blade formed from a plastic material into a unitary structure and adapted to be detachably connected to a handle in an L-shaped configuration, said blade comprising:
   a. a rigid, lower tongue engaging flange section extending along the length thereof;
   b. an upper teeth engaging flange section; and
   c. a web having a relatively thin upstanding wall interconnecting the upper and lower flanges which extend laterally from the web and which are integral therewith, said wall having one or more areas of weakness which provide the web with sufficient flexibility so that when the upper teeth engaging flange is urged into contact with a patient's teeth during examination of a patient's larynx, the web will flex or bend, thereby relieving the pressure applied to the patient's teeth by the upper flange and thereby avoiding damaging the patient's teeth.

2. The laryngoscope blade of claim 1, wherein the upstanding wall of the web is weakened in at least one area by a longitudinal groove.

3. The laryngoscope blade of claim 1, wherein the upstanding wall of the web is weakened in at least one area by an elongated window.

4. The laryngoscope blade of claim 1, wherein the upstanding wall of the web is weakened in at least one area by a thinned webbed section.

5. A laryngoscope including in combination:
 a. an elongated handle provided with a light source at the proximal end thereof;
 b. a detachable, non-metallic blade formed from a plastic material into a unitary structure comprising a rigid, lower tongue engaging flange section, an upper teeth engaging flange section extending along the length thereof, and a web having an upstanding, relatively thin wall interconnecting the upper and lower flanges which are formed integral therewith, said wall having one or more areas of weakness which provide the web with sufficient flexibility so that when the upper teeth engaging flange is urged into contact with a patient's teeth during examination of the patient's larynx, the web will flex or bend, thereby relieving the pressure applied to the patient's teeth by the upper flange and thereby avoiding damaging the patient's teeth; and
 c. means to connect the blade to the end of the handle in an L-shaped configuration.

6. The laryngoscope of claim 5, wherein the blade is provided with a light conductor to conduct light from the light source in the handle to the distal end of the blade.

* * * * *

UNITED STATES PATENT AND TRADEMARK OFFICE
CERTIFICATE OF CORRECTION

PATENT NO. : 4,570,614

DATED : February 18, 1986

INVENTOR(S) : Jack Bauman

It is certified that error appears in the above-identified patent and that said Letters Patent is hereby corrected as shown below:

Column 2, line 38, delete "the" first occurrence.

Column 3, line 3, delete "or" and insert therefor --of--.

Column 5, line 61, delete "Afer" and insert therefor --After--.

Column 6, line 33, delete "maaterial" and insert therefor --material--.

Column 6, line 36, delete "cann" and insert therefor --can--.

Column 8, line 5, after "which" insert --extend laterally from the web and which--.

Signed and Sealed this

Twenty-fourth Day of June 1986

[SEAL]

Attest:

DONALD J. QUIGG

Attesting Officer

Commissioner of Patents and Trademarks